US011084062B2

(12) United States Patent
Loebl et al.

(10) Patent No.: US 11,084,062 B2
(45) Date of Patent: Aug. 10, 2021

(54) ULTRASOUND TRANSDUCER ARRAY, PROBE AND SYSTEM

(71) Applicant: KONINKLIJKE PHILIPS N.V., Eindhoven (NL)

(72) Inventors: Hans-Peter Loebl, Eindhoven (NL); Alfons Wouter Groenland, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 586 days.

(21) Appl. No.: 15/770,605

(22) PCT Filed: Nov. 2, 2016

(86) PCT No.: PCT/EP2016/076316
§ 371 (c)(1),
(2) Date: Apr. 24, 2018

(87) PCT Pub. No.: WO2017/076843
PCT Pub. Date: May 11, 2017

(65) Prior Publication Data
US 2018/0310916 A1 Nov. 1, 2018

(30) Foreign Application Priority Data
Nov. 2, 2015 (EP) ..................................... 15192480

(51) Int. Cl.
B06B 1/02 (2006.01)

(52) U.S. Cl.
CPC .......... B06B 1/0292 (2013.01); B06B 1/0215 (2013.01); B06B 2201/40 (2013.01); B06B 2201/51 (2013.01); B06B 2201/76 (2013.01)

(58) Field of Classification Search
CPC ........... A61B 8/00; A61B 8/4483; B06B 1/02; B06B 1/0215; B06B 1/0292; B06B 2201/40; B06B 2201/76; B06B 2201/51
See application file for complete search history.

(56) References Cited

U.S. PATENT DOCUMENTS 3,296,360 A * 1/1967 Faler .................... H05K 1/0293
174/254
4,442,473 A * 4/1984 Holtzman ................ H01G 4/38
361/275.4

(Continued)

FOREIGN PATENT DOCUMENTS

CN 1886006 A 12/2006
CN 102520032 A 6/2012
(Continued)

OTHER PUBLICATIONS

Gaynor Color in the Corners: ITO-Free White OLEDs with Angular Color Stability (Year: 2013).*

(Continued)

Primary Examiner — Isam A Alsomiri
Assistant Examiner — Amie M Ndure

(57) ABSTRACT

An ultrasound transducer array is provided that comprises a plurality of CMUT (capacitive micromachined ultrasound transducer) cells (100), each CMUT cell comprising a substrate (300) carrying a first electrode (110) of a first electrode arrangement, the substrate being spatially separated from a flexible membrane including a second electrode (120) of a second electrode arrangement by a gap (130), at least one of the first electrode and the second electrode being electrically insulated from said gap by at least one dielectric layer (311, 313), wherein at least one of the first electrode arrangement and the second electrode arrangement is partitioned into a plurality of sections interconnected by respec- (Continued)

tive fuse portions (112, 122). An ultrasound probe and an ultrasound system comprising such an ultrasound transducer array are also disclosed.

13 Claims, 10 Drawing Sheets

(56) References Cited

U.S. PATENT DOCUMENTS

| | | |
|---|---|---|
| 5,997,479 A | 12/1999 | Savord |
| 6,013,032 A | 1/2000 | Savord |
| 6,283,919 B1 | 9/2001 | Roundhill et al. |
| 6,443,896 B1 | 9/2002 | Detmer |
| 6,458,083 B1 | 10/2002 | Jago et al. |
| 6,530,885 B1 | 3/2003 | Entrekin et al. |
| 6,623,432 B2 | 9/2003 | Powers et al. |
| 7,741,686 B2 | 6/2010 | Khuri-Yakub et al. |
| 7,817,811 B2 | 10/2010 | Umemura et al. |
| 9,319,800 B2 | 4/2016 | Hong et al. |
| 2004/0190377 A1 | 9/2004 | Lewandowski et al. |
| 2005/0119575 A1 | 6/2005 | Ladabaum et al. |
| 2006/0145059 A1* | 7/2006 | Lee ........................ H04R 23/00 250/214 R |
| 2008/0194053 A1* | 8/2008 | Huang .................. B06B 1/0292 438/53 |
| 2008/0290756 A1* | 11/2008 | Huang ............... G01N 29/2406 310/300 |
| 2009/0152980 A1* | 6/2009 | Huang ............... G01N 29/2406 310/309 |
| 2009/0167107 A1* | 7/2009 | Huang .................. H03H 9/2405 310/300 |
| 2010/0255623 A1* | 10/2010 | Huang .................. H01L 25/042 438/51 |
| 2011/0050033 A1 | 3/2011 | Nikoozadeh et al. |
| 2011/0272693 A1 | 11/2011 | Kobayashi et al. |
| 2012/0123268 A1 | 5/2012 | Tanaka et al. |
| 2013/0135971 A1 | 5/2013 | Nakanishi |
| 2016/0310992 A1* | 10/2016 | Van Rens ............ A61B 8/4444 |

FOREIGN PATENT DOCUMENTS

| | | |
|---|---|---|
| CN | 104837096 A | 8/2015 |
| EP | 1003229 A1 | 5/2000 |
| EP | 2697160 B1 | 2/2014 |
| EP | 2881182 A2 | 6/2015 |
| WO | 2007009118 A2 | 1/2007 |
| WO | 2010097729 A1 | 9/2010 |
| WO | 2015139979 A1 | 9/2015 |

OTHER PUBLICATIONS

Connolly et al High Density Capacitor Development at ABB Power, IEEE Conference on Conduction and Breakdown in Solid Dielectrics, Jun. 22-25 Vasteras, Sweden (1998).

* cited by examiner

ULTRASOUND TRANSDUCER ARRAY, PROBE AND SYSTEM

This application is the U.S. National Phase application under 35 U.S.C. § 371 of International Application No. PCT/EP2016/076316, filed on Nov. 2, 2016, which claims the benefit of EP Application Serial No. 15192480.0, filed Nov. 2, 2015. These applications are hereby incorporated by reference herein.

FIELD OF THE INVENTION

The present invention relates to an ultrasound transducer array comprising a plurality of CMUT (capacitive micromachined ultrasound transducer) cells, each CMUT cell comprising a substrate carrying a first electrode of a first electrode arrangement, wherein at least part of the substrate being spatially separated from a flexible membrane including a second electrode of a second electrode arrangement by a gap, at least one of the first electrode and the second electrode being electrically insulated from said gap by at least one dielectric layer.

The present invention further relates to an ultrasound probe comprising such an ultrasound transducer array.

The present invention yet further relates to an ultrasound system comprising such an ultrasound transducer array and/or ultrasound probe.

BACKGROUND OF THE INVENTION

Capacitive micro-machined ultrasonic transducer (CMUT) devices are rapidly gaining popularity as the sensors in a range of sensing apparatuses such as imaging apparatuses. This is because CMUT devices can offer excellent bandwidth and acoustic impedance characteristics, which makes them the preferable over e.g. piezoelectric transducers.

Vibration of the CMUT membrane can be triggered by applying pressure (for example using ultrasound) or can be induced electrically. Electrical connection to the CMUT device, often by means of an integrated circuit (IC) such as an application specific integrated circuit (ASIC) facilitates both transmission and reception modes of the device. In reception mode, changes in the membrane position cause changes in electrical capacitance, which can be registered electronically. In transmission mode, applying an electrical signal causes vibration of the membrane.

CMUT devices generally operate with a biasing voltage applied. The CMUT can be operated in so called collapsed mode where the biasing voltage applied is increased above the collapse voltage to restrict the membrane and confine part of it against the substrate such that only a part of the substrate is being spatially separated from the flexible membrane. The frequency of operation of the CMUT device is characterised by the material and physical properties of the membrane, such as the stiffness, and the size of the cavity. The bias voltage and application of the CMUT device also influence the operation mode. A CMUT device is often used in apparatuses for ultrasound imaging applications and in other applications where the CMUT device is used to detect fluid or air pressures. A pressure causes a deflection of the membrane that is electronically sensed as a change of capacitance. A pressure reading can then be derived.

FIG. 1 schematically depicts a top view and FIG. 2 schematically depicts a cross-section along the line A-A' in FIG. 1 of a conventional CMUT device. The CMUT device may comprise a plurality of CMUT cells 100, e.g. a CMUT array, in a CMUT region 10 of the device and may further comprise a plurality of interconnects 200, which plurality may include routing lines 205, and may be located in an interconnect region 20 of the device. The boundary between the CMUT region 10 and the interconnect region 20 is indicated by the vertical dashed lines in FIG. 2. The interconnects 200 typically provide an interconnection to a conductive contact 210 such as a bond pad inside the CMUT device. Such conductive contacts may provide a connection to the outside world or may be used to facilitate interconnections between different elements of the CMUT device, e.g. between different CMUT cells 100, between a CMUT cell 100 and a signal processing element, and so on.

Each CMUT cell 100 typically comprises a first electrode 110 separated from a second electrode 120 by a cavity 130. The second electrode 120 is typically embedded in a membrane 140 made of one or more electrically insulating or dielectric layers. Conventional CMUT designs have membrane 140 layer thicknesses in the order of 1-2 micron, which can be processed with common fabrication methods such as plasma-enhanced chemical vapour deposition (PECVD). However, where the CMUT cells 100 are required to operate at a low frequency, the membrane diameter D may need to be in excess of 100 micron, which can result in an increased thickness for the membrane 140, e.g. larger than 3 micron. In some designs, the second electrode 120 is embedded in the membrane 140, i.e. sandwiched in between a relatively thin dielectric layer portion 142 and a relatively thick dielectric layer portion 144 from the cavity 130 to prevent a short circuit between the first electrode 110 and the second electrode 120 upon deformation of the membrane 140 including the second electrode 120 towards the first electrode 110. Additionally or alternatively, the first electrode 110 may be protected by a relatively thin dielectric layer (not shown) to prevent a short circuit between the first electrode 110 and the second electrode 120 upon deformation of the membrane 140 including the second electrode 120 towards the first electrode 110. In some application domains, the CMUT cells 100 may be operated in so-called collapse mode, in which the membrane 140 is in permanent contact with the floor (substrate) of the CMUT cell and is forced to resonate in this collapsed state. This for instance can increase the sensitivity and transmit power of the CMUT cells 100.

When operated in the collapse mode the CMUT cells 100 have to withstand high electrical fields in the order of several MV/cm, e.g. 2-6 MV/cm, between the bottom electrode 110 and the top electrode 120. The protective dielectric layer(s) used in CMUTs may be e.g. SiO2 made by PECVD or other suitable thin film deposition techniques providing good step coverage. However, electrodes typically are not perfectly smooth, e.g. may have a relatively large surface roughness or particles may be present on the electrode receiving surfaces during thin film deposition of the electrodes. Also, there may be defects in the protective dielectric layer(s). Consequently, it is difficult to achieve reliably high electric breakdown fields. This is, however, required for a robust CMUT array in which all CMUT cells 100 should have equally high breakdown fields, or at least have breakdown fields that do not vary by more than an acceptable tolerance.

SUMMARY OF THE INVENTION

The present invention seeks to provide an ultrasound transducer array exhibiting reliably high electric breakdown fields.

The present invention further seeks to provide an ultrasound probe comprising such an ultrasound transducer array.

The present invention yet further seeks to provide an ultrasound system comprising such an ultrasound probe or ultrasound transducer array.

According to an aspect, there is provided an ultrasound transducer array comprising a plurality of CMUT (capacitive micromachined ultrasound transducer) cells, each CMUT cell comprising a substrate carrying a first electrode of a first electrode arrangement, wherein at least part of the substrate being spatially separated from a flexible membrane including a second electrode of a second electrode arrangement by a gap, at least one of the first electrode and the second electrode being electrically insulated from said gap by at least one dielectric layer, wherein at least one of the first electrode arrangement and the second electrode arrangement is partitioned into a plurality of sections interconnected by respective fuse portions, wherein the first electrode arrangement comprises a plurality of rows of first electrodes, the first electrodes in each row being interconnected by respective fuse portions; and the second electrode arrangement comprises a plurality of columns of second electrodes, the second electrodes in each column being interconnected by respective fuse portions and wherein each row and column is individually addressable.

The inclusion of fuse portions into the electrode arrangements of the ultrasound transducer array ensures that upon a localized short circuit in one of the sections of the electrode arrangement, this section is isolated from the rest of the electrode arrangement due to the fact that a localized high current associated with the short circuit will cause the fuse portions that separate this section from the rest of the electrode arrangement will blow, thereby rendering the short circuited section isolated from the rest of the electrode arrangement. Consequently, the rest of the electrode arrangement can remain functional and is protected from damage by the localized short circuit by virtue of the fact that the short circuit is electrically isolated from the remainder of the electrode arrangement. Each CMUT cell may be individually addressable in a passive matrix-style addressing scheme by selecting the appropriate row and column. Upon failure of one of the CMUT cells, only the associated row and column will be rendered inoperable by the destruction of the fuse portions that connects the failing CMUT cell to its neighbouring cells in the relevant row and column, such that the remainder of the ultrasound transducer array can remain operational.

In an embodiment, each fuse portion has a sheet resistance not exceeding $1\Omega/\square$. This ensures that during normal operation of the electrode arrangements, current will flow through these fuse portions whilst at the occurrence of a short circuit, these fuse portions will blow, e.g. burn through the like, in order to render the section including the short circuit inoperable. The grid of conductive tracks may exhibit a typical sheet resistance of about $0.1\Omega/\square$, wherein each fuse portion has a sheet resistance exceeding the typical sheet resistance of the grid of conductive tracks.

The at least one dielectric layer may comprise a first dielectric layer in between the gap and the first electrode and a second dielectric layer in between the gap and the second electrode in order to further improve the robustness of the CMUT cell against the occurrence of short circuits.

The fuse portions may have any suitable shape that will allow the fuse portion to fail before any other region of the electrode arrangement, such as a shape in which the fuse portion has a smaller width than the portion of the electrodes arrangement the fuse portion is connected to. For example, each fuse portion may be strip-shaped, in which the fuse portion may be shaped as a conductive track having a smaller width than the conductive track in which the fuse portion is placed or may be bow tie-shaped, i.e., define a pinch point in a conductive track of the electrode arrangement.

According to another aspect, there is provided an ultrasound probe comprising the ultrasound transducer array of any of the above embodiments. Such an ultrasound probe benefits from an increased robustness and lifetime due to the fact that a short circuit in the ultrasound transducer array does not necessarily lead to the catastrophic failure of the entire array as explained above.

According to yet another aspect, there is provided an ultrasound system comprising the ultrasound transducer array or the ultrasound probe of any of the previous embodiments, the ultrasound system further comprising a power supply conductively coupled to the first electrode arrangement and the second electrode arrangement. Such an ultrasound system may be an ultrasound diagnostic imaging system, in which case the system is typically adapted to transmit imaging pulses and receive imaging pulse echoes, or may be an ultrasound therapeutic system, in which case the system may be adapted to transmit a sequence of high-energy ultrasound pulses, for example to destroy damaged or diseased tissue in a patient.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
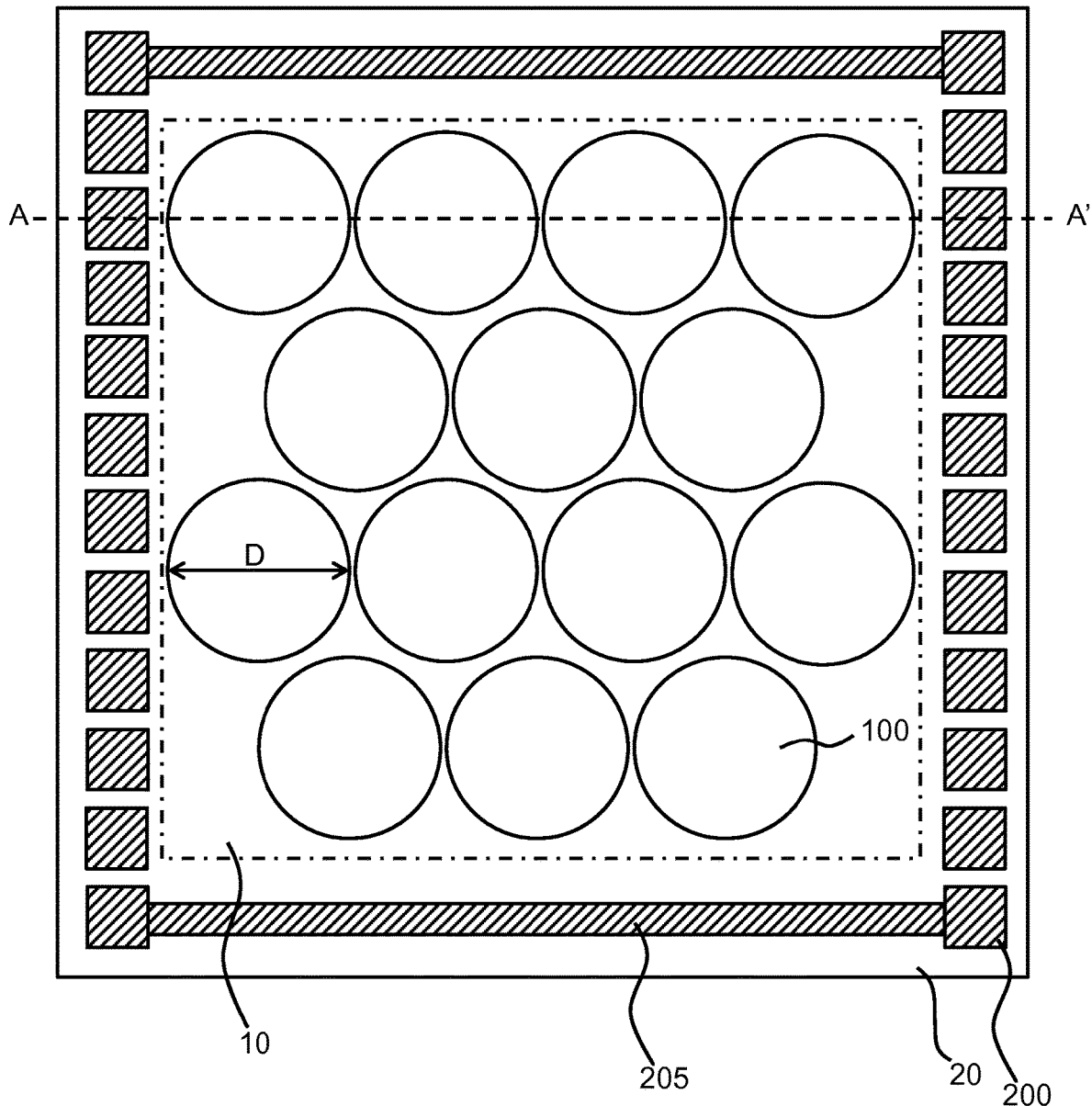
FIG. 1 schematically depicts a top view of a known CMUT transducer array.

It should be understood that the Figures are merely schematic and are not drawn to scale. It should also be understood that the same reference numerals are used throughout the Figures to indicate the same or similar parts.

Figure 3:
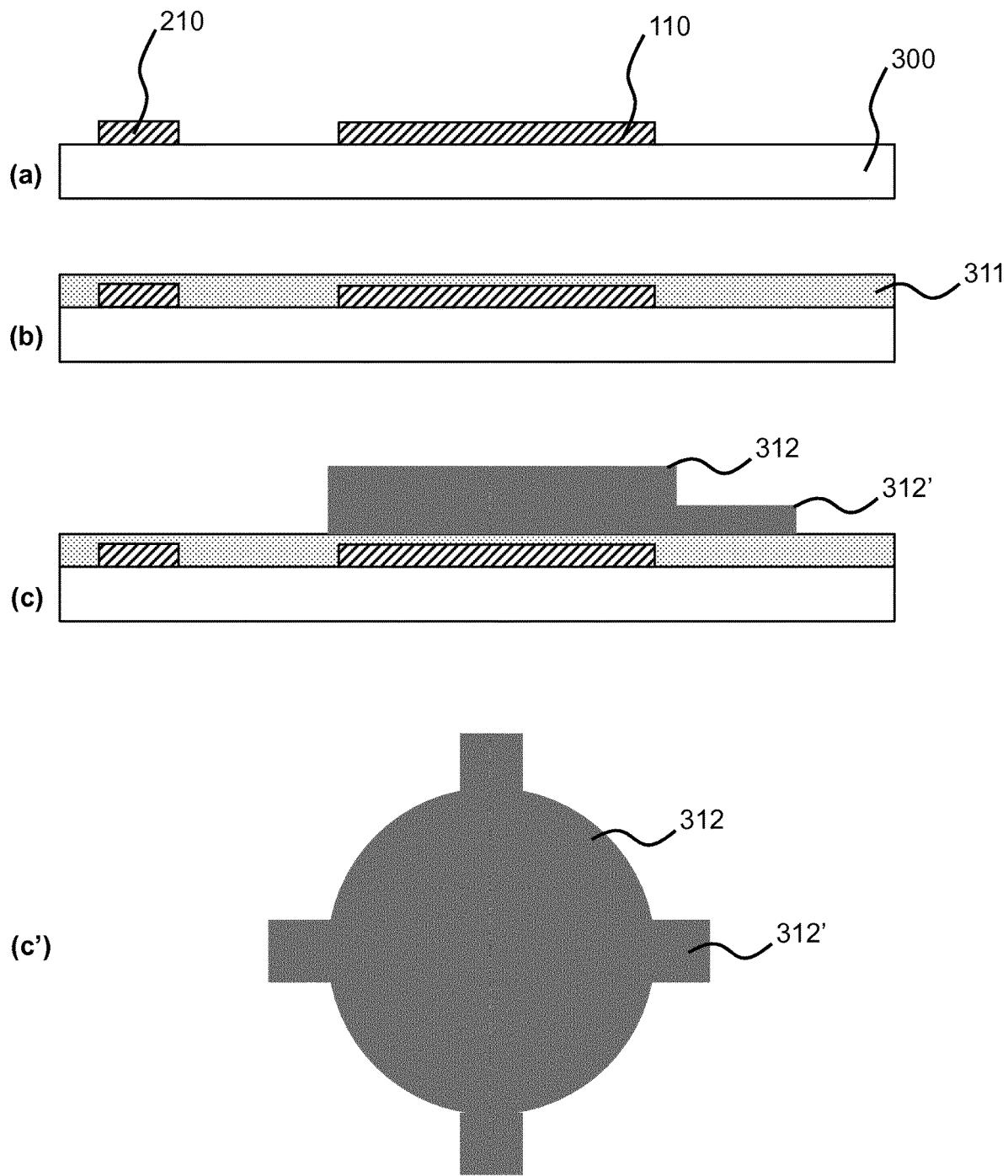
FIG. 3 schematically depicts a method of manufacturing a CMUT array according to an embodiment.
Figure 3:
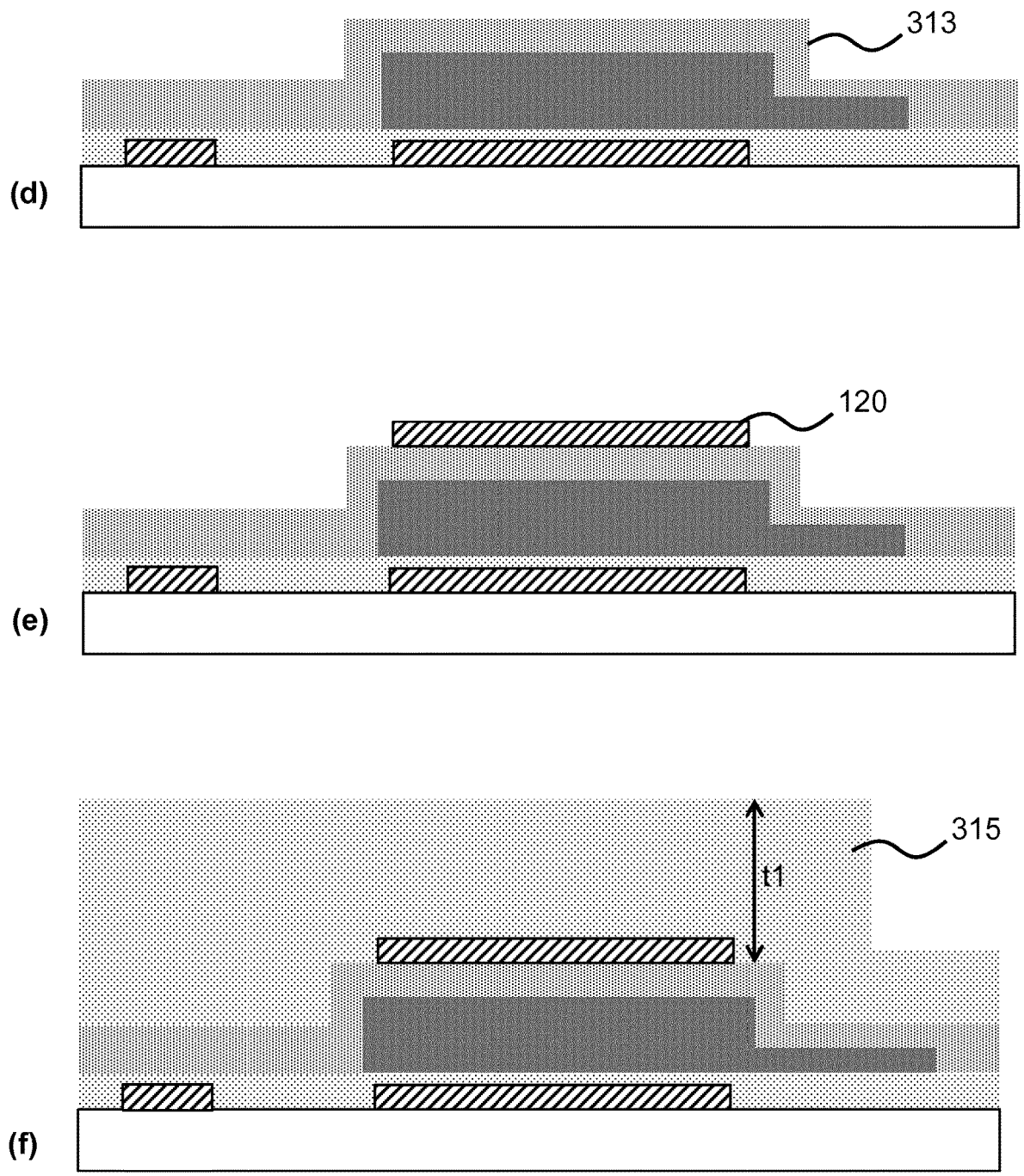
Figure 3:
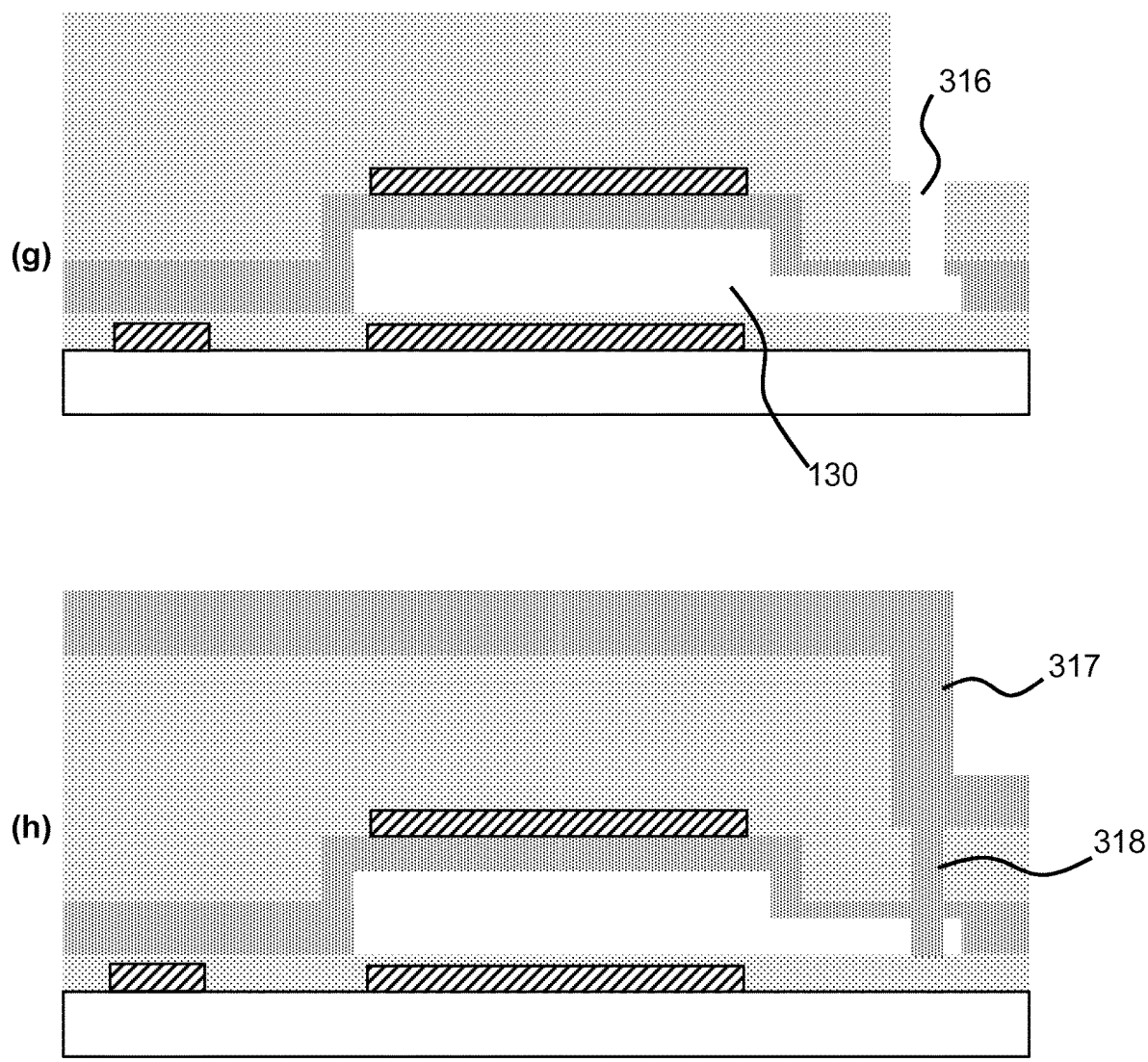

FIG. 3 schematically depicts a non-limiting example embodiment of a CMUT transducer array manufacturing method. The method proceeds in step (a) with the provision of a substrate 300, which may be any suitable substrate such as a silicon substrate, a silicon-on-insulator substrate, a silicon germanium substrate, a gallium nitride substrate and so on. A silicon-based substrate may for instance be used in a CMOS manufacturing process. The substrate 300 may comprise several structures, such as semiconductor devices, a metallization stack interconnecting the semiconductor devices and/or the CMUT cells, a passivation stack over the metallization stack and so on. The substrate 300 may for instance be the substrate of an application specific integrated circuit (ASIC) including the CMUT cells 100 on its layer stack, e.g. passivation and/or planarization stack, wherein the CMUT cells 100 may be connected to signal processing circuitry on the substrate 300 by the metallization stack. The provision of such substrates 300 is well-known per se and belongs to the routine skills of the skilled artisan such that the provision of suitable substrates 300 will not be discussed in further detail for the sake of brevity only.

A first electrode 110 is formed on the substrate 300, which electrode may be formed from any suitable electrically conductive material, e.g. metals or metal alloys, doped semiconductor materials such as doped poly-silicon, (semi) conducting oxides and so on. It is for instance particularly advantageous to use metals that are readily available in the manufacturing technology of choice, as this requires minimal redesign of the manufacturing flow, which is attractive from a cost perspective. For example, in a CMOS process, conductive materials such as Al, W, Cu, Ti, TiN and so on, as well as combinations of such materials, may be used to form the first electrode 110.

In accordance with an embodiment of the present invention, the formation of the first electrode 110 forms part of the formation of a first electrode arrangement over the substrate 300, which first electrode arrangement includes the respective first electrodes 110 of the CMUT cells 100. As will be explained in more detail below, the first electrode arrangement is partitioned into a plurality of regions that are electrically interconnected by respective fuse portions designed to blow upon a connected region of the first electrode arrangement encountering a short circuit, such that the localized high currents associated with such a short circuit cannot spread to neighbouring sections of the first electrode arrangement, thereby protecting these neighbouring sections from becoming damaged by these high currents. The fuse regions may be formed by appropriate dimensioning of the corresponding parts of the first electrode arrangement. This for instance may be simply achieved by the application of a corresponding mask design used to deposit or pattern the conductive materials used to form the first electrode arrangement.

A conductive contact 210 may be formed on the substrate 30 at the same time, which may be made of the same material as the first electrode arrangement including first electrodes 110, e.g. by patterning a deposited metal or metal alloy layer to form the one or more first electrodes 110 and one or more bond pads. The conductive contact 210 is not necessarily a bond pad but may take any suitable shape, e.g. if the conductive contact 210 is to provide a contact for (internal) I/O routing purposes as previously mentioned. The formation of the conductive contact 210 may be omitted from this step if the bond pad 210 is to be provided in a different layer, e.g. in a top layer of a metallization stack (not shown) of the substrate 300, in the layer defining the second electrode arrangement including second electrodes 120 as will be explained in more detail later, and so on.

The first electrode 110, the (optional) conductive contact 210 and the substrate 300 may subsequently optionally be covered by an electrically insulating material layer 311. This is shown in step (b). Electrically insulating layers will also be referred to as dielectric layers in the present application. Such a dielectric layer 311 for instance may be used to electrically insulate the first electrode 110 from its counter electrode 120 (see below) to reduce the risk of short circuits between the electrodes during the operation of the CMUT device. In addition, the dielectric layer 311 may be used to protect the first electrode 110 and the substrate 300 from damage during the removal of the sacrificial material to form the cavity over the first electrode 110.

Although the dielectric layer 311 is shown to cover the entire substrate surface 300, it is equally feasible to provide a patterned dielectric layer 311 in which only certain parts of the substrate 300 together with the first electrode 110 are covered by the dielectric layer 311. Any suitable dielectric material may be used for the protection of the first electrode 110 and the substrate 300, e.g. one or more materials selected from silicon nitride ($Si_3N_4$), silicon oxide ($SiO_2$), aluminium oxide ($Al_2O_3$), hafnium oxide ($HfO_2$) or the like, although it is emphasized that the suitable dielectric materials are not limited to these example materials. In addition, mixtures or laminates of the aforementioned dielectric materials may be used for the protection of the first electrode 110. As such a dielectric layer 311 may be formed in any suitable manner, e.g. using suitable deposition techniques such as LAD, (PE)ALD, PLD, PVD, LPCVD and PECVD, its formation will not be explained in further detail for the sake of brevity.

In step (c), a sacrificial material is formed, e.g. through a suitable deposition technique, on the substrate 300 including the first electrode 110 and the optional dielectric layer 311. The sacrificial material is patterned to form a first portion 312 from which the cavity is formed and may further comprise a second portion 312' acting as a channel through which the sacrificial material is removed. The height of the first portion 312 and the second portion 312' of the sacrificial material corresponding to the gap height of the cavity to be formed is typically in the range of 100-1,000 nm although it should be understood that values outside this range may also be contemplated.

In an embodiment, the first portion 312 is deposited as a circular portion having a few teeth-like protrusions as the second portion 312', e.g. 2-8 of such protrusions. A top-view of such a sacrificial material portion is shown in step (c'), in which four of such protrusions are shown by way of non-limiting example only. The teeth-like second portions 312' are typically used as cavity access platforms outside the membrane to be formed through which access to the first portion 312 can be provided for opening or releasing the cavity. It should be understood that the first portion 312 and the second portion 312' are typically formed to the same thickness or height, with the membrane to be formed extending towards the substrate 300 in between the teeth-like second portions 312'. In the various drawings of the present application, the second portions 312' are shown to have a different thickness in order to indicate this aspect, i.e. the aspect that the membrane of the CMUT device extends towards the substrate 300 in between the teeth-like second portions 312'. This should not be construed as the first portion 312 and the second portion 312' having different thicknesses in reality.

In principle, any suitable sacrificial material may be used, although for device performance reasons it is preferable to use sacrificial materials that can be effectively removed in a subsequent etching step. For instance, the use of metals such as Al, Cr and Mo, Ti and (Ti)W or non-metals such as amorphous silicon or silicon oxide may be contemplated. Materials such as Al, amorphous silicon and silicon oxide are for instance readily available in CMOS processes, and of these materials Al can be particularly effectively removed by etching. The patterned sacrificial material may be formed in any suitable manner, e.g. using suitable deposition and patterning techniques and its formation will not be explained in further detail for the sake of brevity.

It will be understood that the diameter of the first portion 312 defines the diameter of the cavity of a CMUT cell 100 to be formed. In an embodiment, the diameter is selected in a range of 20-500 micron, more preferably in a range of 50-300 micron, although it should be understood that larger diameters may also be contemplated, e.g. diameters up to 1,000 micron.

In step (d), a first dielectric layer 313 of the membrane to be formed is deposited over the first portion 312 and the second portion 312' of the sacrificial material and the exposed portions of the dielectric layer 311 if present. As the first dielectric layer 313 and the dielectric layer 311 are both exposed to the etch recipe for removing the sacrificial layer, the first dielectric layer 313 and the dielectric layer 311 may be of the same material, although it is of course also plausible to use different materials for the first dielectric layer 313 and the dielectric layer 311 respectively. In an embodiment, the first dielectric layer 313 and the dielectric layer 311 each comprise at least one layer formed any suitable dielectric material, such as a silicon oxide layer, e.g., $SiO_2$, a silicon nitride layer, e.g., $Si_3N_4$ or the like, an aluminium oxide ($Al_2O_3$) layer, a hafnium oxide ($HfO_2$) layer and so on. Many other suitable dielectric layer materials will be apparent to the skilled person. The first dielectric layer 313 may be formed as a layer stack, e.g. an oxide-nitride stack or an oxide-nitride-oxide stack. Similarly, the optional dielectric layer 311 may be formed as such a stack. It is reiterated that any suitable dielectric material may be used for the optional dielectric layer 311 and the first dielectric layer 313. In addition, mixtures or laminates of the aforementioned dielectric materials may be used for these dielectric layers.

After the formation of the first dielectric layer 313, the second electrode arrangement including the second electrodes 120 is formed on the first dielectric layer 313 as shown in step (e) such that each second electrode 120 is oriented opposite a first electrode 110. The second electrode arrangement preferably is formed of the same electrically conductive material as the first electrode arrangement, although it should be understood that the second electrode arrangement and the first electrode arrangement alternatively may be formed of different materials. The second electrode arrangement may for instance be formed from any suitable electrically conductive material such as Al, W, Cu, Ti, TiN and so on, as well as combinations of such materials. The second electrode arrangement may be formed using well-known techniques that are not further explained for the sake of brevity only. The first electrode arrangement and the second electrode 120 may be formed to any suitable thickness, e.g. 200-700 nm thickness.

In an embodiment of the present invention, the second electrode arrangement is partitioned into a plurality of regions that are electrically interconnected by respective fuse portions designed to blow upon a connected region of the second electrode arrangement encountering a short circuit, such that the localized high currents associated with such a short circuit cannot spread to neighbouring sections of the second electrode arrangement, thereby protecting these neighbouring sections from becoming damaged by these high currents. The fuse regions may be formed by appropriate dimensioning of the corresponding parts of the second electrode arrangement. This for instance may be simply achieved by the application of a corresponding mask design used to deposit or pattern the conductive materials used to form the second electrode arrangement. Both the first electrode arrangement and the second electrode arrangement may comprise such fuse portions partitioning each arrangement into a plurality of sections. Alternatively, only one of the first electrode arrangement and the second electrode arrangement may comprise such fuse portions.

After the formation of the second electrode 120, the method proceeds as shown in step (f), in which the second dielectric layer 315 is formed. In an optional embodiment, the second dielectric layer 315 is formed to a first thickness t1, which exceeds the thickness of the first portion 312 of the sacrificial material in between the first electrode 110 and the second electrode 120 such that upon formation of the cavity 130 the height g of the cavity gap is substantially smaller than the thickness t1, i.e. $g/t1 \ll 1$. Preferably $t1 \geq 5\ g$. This ensures that during the release of the cavity 130 in step (g), i.e. by formation of the access or via 316 and the subsequent removal of the first portion 312 and the second portion 312' of the sacrificial material, the membrane exhibits excellent membrane robustness during the cavity release step as $g \ll t1$ at the stage of removal of the sacrificial material to form the cavity 130. Moreover, because the second dielectric layer 315 is formed, e.g. deposited, prior to the release of the cavity 130, a membrane with excellent flatness characteristics is obtained as the presence of the sacrificial material prevents deformation of the first dielectric layer 313 during the formation of the second dielectric layer 315.

The first portion 312 and the second portions 312' of the sacrificial material are subsequently removed as shown in step (g) by the formation of the access or via 316 using a suitable etch recipe to form the cavity 130 in between the first electrode 110 and the second electrode 120 embedded in between the first dielectric layer 313 and the second dielectric layer 315 of the membrane 140 of the CMUT device. Suitable etch recipes for such conventional sacrificial materials are well-known per se and the skilled person will have no difficulty selecting an appropriate etch recipe using his common general knowledge.

The thickness of the dielectric layer stack including the membrane 140 is further increased during the sealing of the access or via 316 in step (h) by the formation of the further dielectric layer 317 including the plug 318 in the access or via 316. The further dielectric layer 317 may be substantially thinner than the second dielectric layer 315. The further dielectric layer 317 may be formed to a thickness of at least twice the height of the cavity 130 to effectively seal the access or via 316.

At this point it is emphasized that steps (a)-(h) schematically depict an advantageous but non-limiting example of forming one or more CMUT cells 100 on a substrate 300. Many alternative routes will be apparent to the skilled person. In particular, it is noted that the following steps are not specific to the embodiment depicted in steps (a)-(h) and may be applied to any CMUT manufacturing process in which a dielectric layer stack includes a CMUT region 10 in which the membranes 140 of the CMUT device are defined and an interconnect region 20 covering the bond pads 200 of the CMUT device.

A notable process variation is that the access or via 316 may be sealed in any suitable manner using any suitable material, e.g. by depositing and patterning a dedicated sealing layer such as a metal or dielectric layer to form the plug 318. It is furthermore noted that the cavity 130 may be released at any suitable point in the CMUT manufacturing process, e.g. prior to the formation of the second dielectric layer 315. Another notable process variation is that the first electrode 110 and/or the second electrode 120 may or may not be separated from the cavity 130 by a dielectric layer, as this is a typical design choice. As previously mentioned, a dielectric layer, i.e. an electrically insulating layer, may be provided over the first electrode 110 and/or the second electrode 120 to prevent direct contact between the first electrode 110 and the second electrode 120 during operation of the CMUT cell 100. The membrane 140 may be formed in any suitable manner, e.g. by a single dielectric layer rather than a stack of dielectric layers, and so on. Such process choices fall within the routine skills of the skilled person and will therefore not explicitly mentioned in detail for the sake of brevity only.

Moreover, it is noted that the bond pads 200, if present, may be formed in any suitable manner as is well-known per se to a person skilled in the art. This is not particularly relevant to the teachings of the present invention and is therefore not described in further detail for the sake of brevity only.

Also, it should be understood that alternative designs of the individual CMUT cells 100 are of course equally feasible. The design of the CMUT cells 100 is not particularly relevant to the present invention, and any suitable design of the cells may be contemplated; for example, 3-electrode CMUT cells 100 in which an intermediate electrode is located between the bottom electrode 110 and the cavity 130 are equally feasible. Such 3-electrode CMUT cells for instance may be contemplated to provide a stimulus and a bias voltage through separate electrodes, e.g. to reduce the risk of membrane sticking to the bottom of the CMUT cell.

At this point it is further noted that although not shown in the various embodiments, it should be understood that the CMUT cells 100 manufactured in accordance with embodiments may comprise additional circuit elements, which may be integrated on the substrate 300 or may be provided on a separate substrate and integrated into a single package with one or more of the CMUT devices from a wafer manufactured in accordance with embodiments of the present invention. Such additional circuitry may be instance be an IC, e.g. an ASIC, for controlling the one or more CMUT cells 100 and/or processing the signals generated by the one or more CMUT cells 100, e.g. to control transmission and/or reception modes of the one or more CMUT cells 100. Other suitable embodiments of the CMUT cells 100 and/or ultrasound transducer array comprising such cells will be immediately apparent to the skilled person.

It is furthermore noted that in the aforementioned manufacturing process, a wafer processed during the manufacturing process may contain a single die, i.e. a single device, in which case the substrate 300 corresponds to the wafer, or a plurality of dies that may be singulated in any suitable manner, e.g. diced, after the completion of the device manufacturing process, in which case the substrate 300 corresponds to a part of the wafer. The interconnection region 200 may be peripheral to a substrate and/or to the wafer as a whole.

Although the optional dielectric layer 311 and the first dielectric layer 313 provide electrical insulation between the first electrode 110 and the second electrode 120, it is difficult to rule out the occurrence of a short circuit between these electrodes during the lifetime of a CMUT cell 100, in particular where such a CMUT cell is operated in collapse mode. In collapse mode, the membrane 130 of the CMUT cell 100 is forced onto the substrate 300 during the entire operation cycle of the CMUT cell 100, typically using a bias voltage exceeding the collapse threshold voltage of the CMUT cell 100. The size of the contact area between the membrane 130 and the substrate 300 is typically governed by the magnitude of the bias voltage. The resonance frequency of the collapsed membrane 130 is a function of this contact area, which property may be exploited in a transmit mode of the ultrasound transducer array by employing a stimulus, e.g. as a modulation on the bias voltage, to the collapsed CMUT cell 100 having a frequency corresponding to the resonance frequency of the collapsed membrane 130 or by controlling the contact area between the collapsed membrane 130 and the substrate 300 in a receive mode of the ultrasound transducer array such that the resonance frequency of the collapsed membrane 130 corresponds to a center frequency of a pulse echo to be received by the collapsed CMUT cell 100 in its receive mode. In this manner, the output pressure and reception sensitivity of the CMUT cells 100 in the ultrasound transducer array may be optimized.

The collapse stresses applied to the membrane 130 may cause defects to appear in the dielectric layer(s) electrically isolating the first electrode 110 from the second electrode 120 in a CMUT cell 100 of the ultrasound transducer array during its lifetime. Such defects can cause a short circuit between the first electrode 110 and the second electrode 120. Other sources of such defects may be pinholes in the dielectric layer(s) electrically isolating the first electrode 110 from the second electrode 120 or imperfect step coverage of the electrodes by a dielectric layer, for example because of limitations in the deposition technique or because of contaminants on the electrode material, e.g. grains or particles prohibiting satisfactory step coverage of the electrode by a dielectric layer. Such defects can lead to electrical breakdown of the CMUT cell 100 and neighbouring CMUT cells in conductive contact with the CMUT cell 100, e.g. through the first and/or second electrode arrangements. This can lead to the catastrophic failure of substantial parts of the ultrasound transducer array, thereby rendering the array no longer fit for purpose.

Embodiments of the present invention seek to electrically isolate short circuits in a particular location of the ultrasound transducer array, i.e. in a particular CMUT cell 100, from the rest of the array such that the ultrasound transducer array remains operable in a satisfactory manner, that is, the regions of the ultrasound transducer array surrounding the region including the short circuit remain unaffected by this short circuit. As a typical ultrasound transducer array comprises hundreds or thousands of CMUT cells 100, this can be compared to the loss of the pixel in a display device, with the loss of a single pixel (or here a single CMUT cell 100 or group of CMUT cells 100) does not affect the overall performance of the device (here the ultrasound transducer array).

Figure 4:
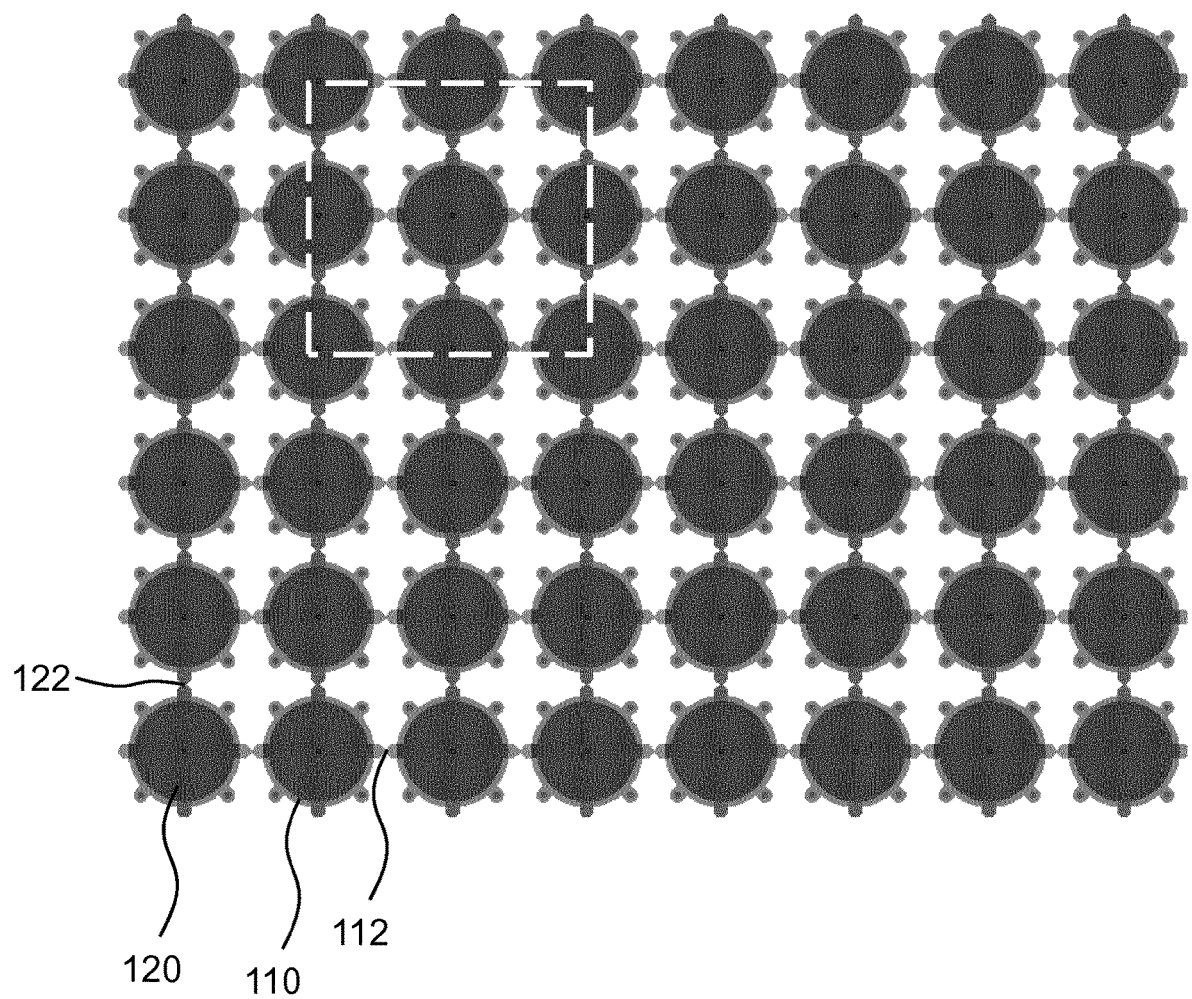
FIG. 4 schematically depicts a top view of a CMUT transducer array according to an embodiment.

FIG. 4 schematically depicts a top view of a first embodiment of an ultrasound transducer array in which the first electrode arrangement including first electrodes 110 is arranged as a plurality of rows of first electrodes 110, in which within a single row each first electrode 110 is electrically connected to a neighbouring first electrode 110 in the row by a fuse portion 112 and in which the second electrode arrangement including second electrodes 120 is arranged as a plurality of columns of second electrodes 120, in which within a single column each second electrode 120 is electrically connected to a neighbouring second electrode 110 in the column by a fuse portion 122. The fuse portions 112, 122 partition the first and second electrode arrangements respectively into a plurality of regions or sections that are electrically interconnected by these fuse portions.

In the context of the present application, reference to rows and columns is made to simply highlight the fact that in the first electrode arrangement, first electrodes 110 are grouped in a first direction and in the second electrode arrangement, second electrodes 120 are grouped in a second direction that runs perpendicular to the first direction. References to rows and columns should not be construed to mean that a particular direction is necessarily horizontal or vertical. In this context, it would for instance be equally feasible that the first electrodes 110 are grouped in columns and the second electrodes 120 are grouped in rows.

Figure 5:
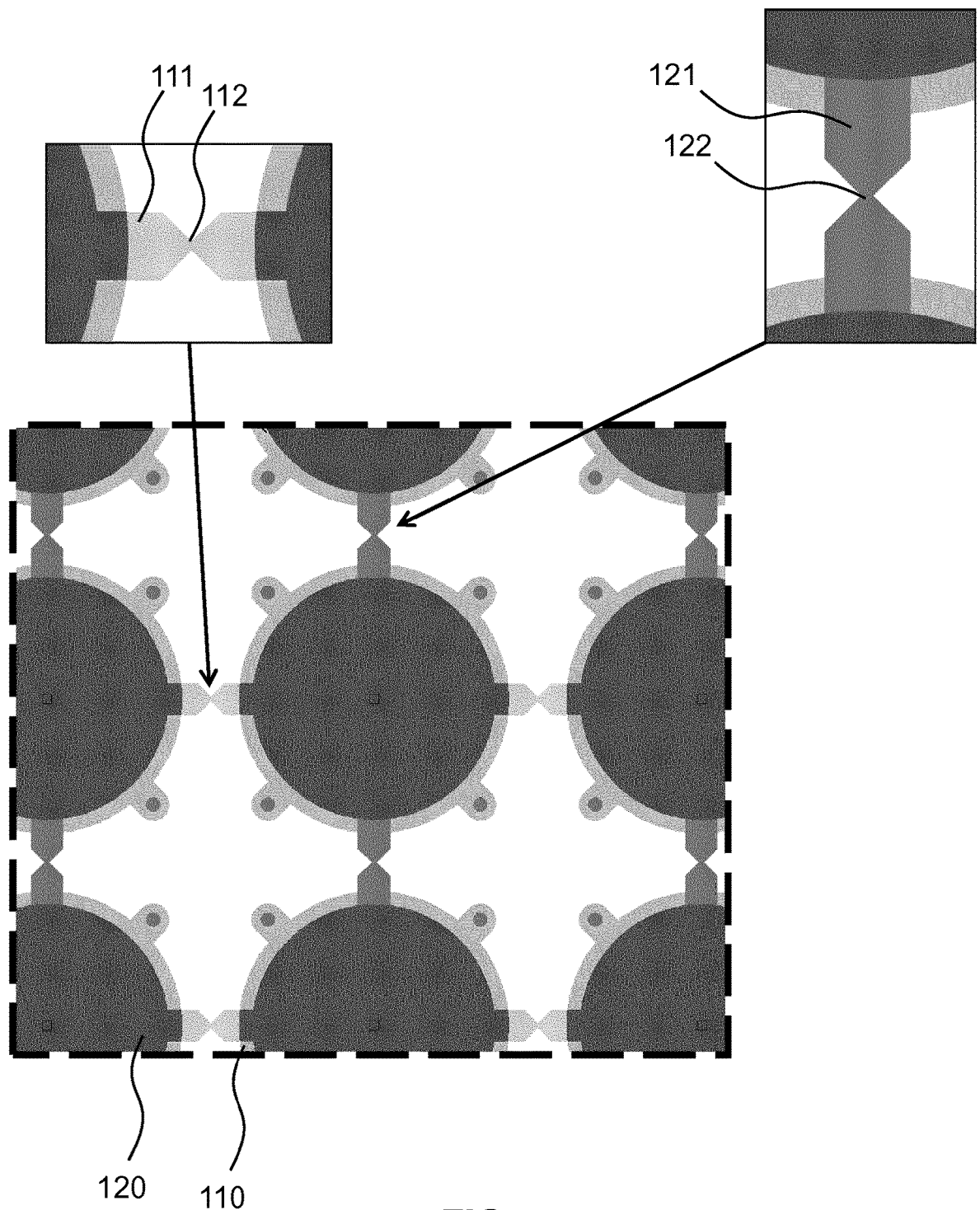
FIG. 5 schematically depicts aspects of the CMUT transducer array of FIG. 4 in more detail.

FIG. 5 schematically depicts a magnification of the portion of the ultrasound transducer array highlighted by the dashed box in FIG. 4. As can be more clearly seen in FIG. 5, the darker second electrodes 120 in the respective columns of the second electrode arrangement are interconnected by fuse portions 122, here shown as a pinch point in conductive tracks 121 interconnecting neighbouring second electrodes 120 in a column of the second electrode arrangement. The lighter first electrodes 110, which are typically located below the second electrodes 120 as explained above, in the respective rows of the first electrode arrangement are interconnected by fuse portions 112, here shown as a pinch point in conductive tracks 111 interconnecting neighbouring first electrodes 110 in a row of the first electrode arrangement. The fuse portions 112, 122 preferably have a sheet resistance not exceeding 1Ω/□ such that the fuse portions 112, 122 do not significantly contribute to the total resistance of the electrode arrangements, for example because many parallel current paths may exist.

During operation, if one of the CMUT cells 100 encounters a short circuit, the increased current between the first electrode 110 and a second electrode 120 of the CMUT cell 100 will cause the fuses 112, 122 to burn through, thereby electrically insulating the CMUT cell 100 from its neighbouring CMUT cells, i.e. the neighbouring CMUT cells in the row of interconnected first electrodes 110 and the neighbouring CMUT cells in the column of interconnected second electrodes 120. This renders these rows and columns inoperable, whilst the remaining rows and columns of the ultrasound transducer array remains operable such that large parts of the ultrasound transducer array can still be used.

In FIGS. 4 and 5, the fuse portions 112 and 122 are located within a conductive track 111, 121 respectively and form a pinch point within these conductive tracks. It should be understood that such a 'bowtie'-shaped design is by way of non-limiting example only; any suitable fuse portion design may be contemplated, such as a design in which each fuse portion is shaped as a further conductive track having a smaller width than the conductive track 111, 121 in which the fuse portion 112, 122 is located to provide a higher resistance portion within the conductive track 111, 121.

The fuse portions 112 and 122 may have any suitable dimension in order to provide the fuse portions with the desired sheet resistance, e.g. a sheet resistance not exceeding 1Ω/□, e.g. a sheet resistance between 0.1-1Ω/□. The fuse portions 112 and 122 may be dimensioned as small as possible, e.g. have the minimum dimensions available in a particular lithography process. By way of non-limiting example, the fuse portions 112 122 may each have dimensions of 0.5 µm in length and 1 µm in width.

In FIGS. 4 and 5, each of the first electrode arrangement and the second electrode arrangement are partitioned into multiple regions by respective fuse portions 112, 122. However, this is by way of non-limiting example only and it is equally feasible that only one of the first electrode arrangement and the second electrode arrangement is partitioned in this manner.

Figure 6:
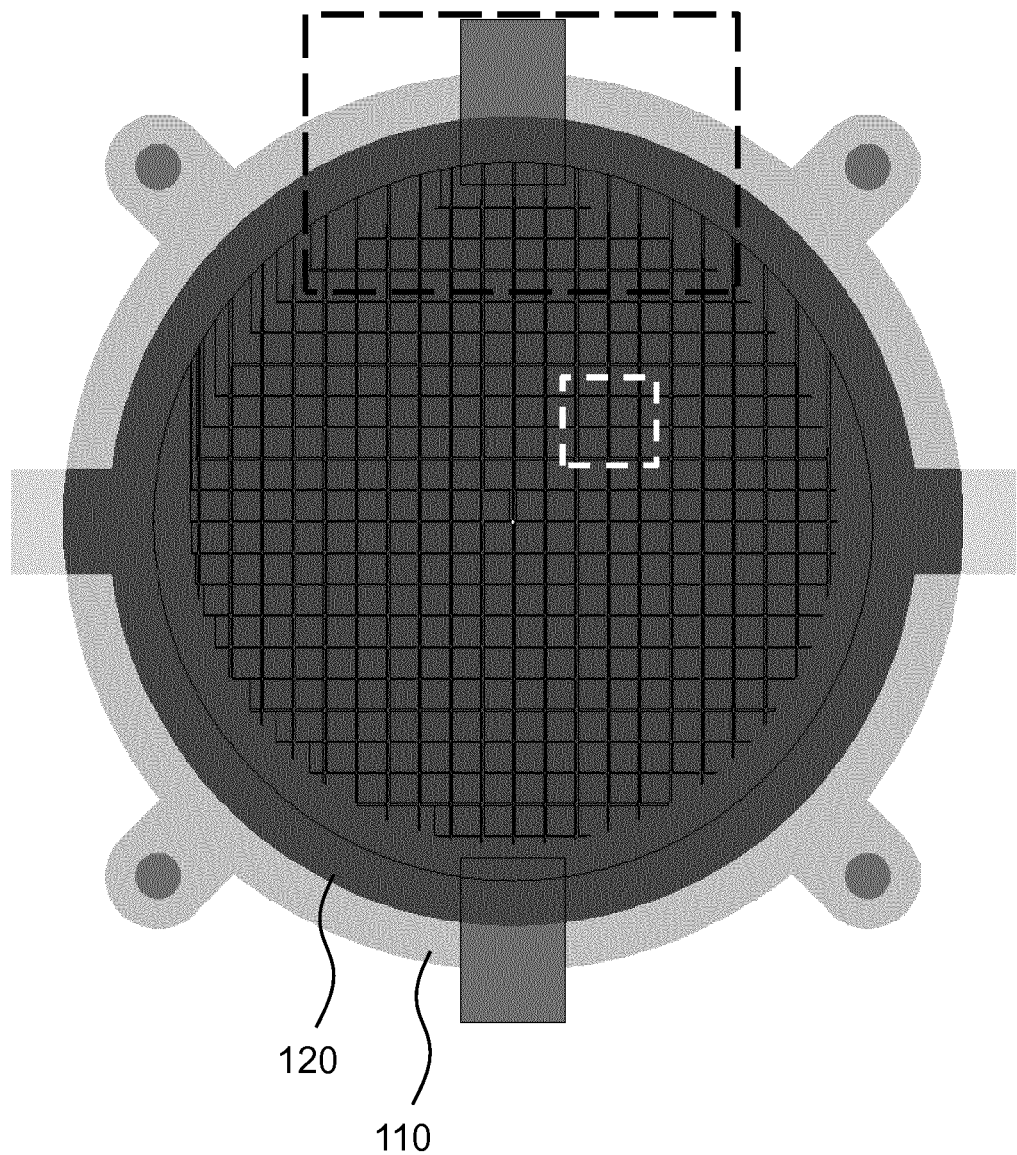
FIG. 6 schematically depicts a top view of a CMUT transducer array according to another aspect.
Figure 7:
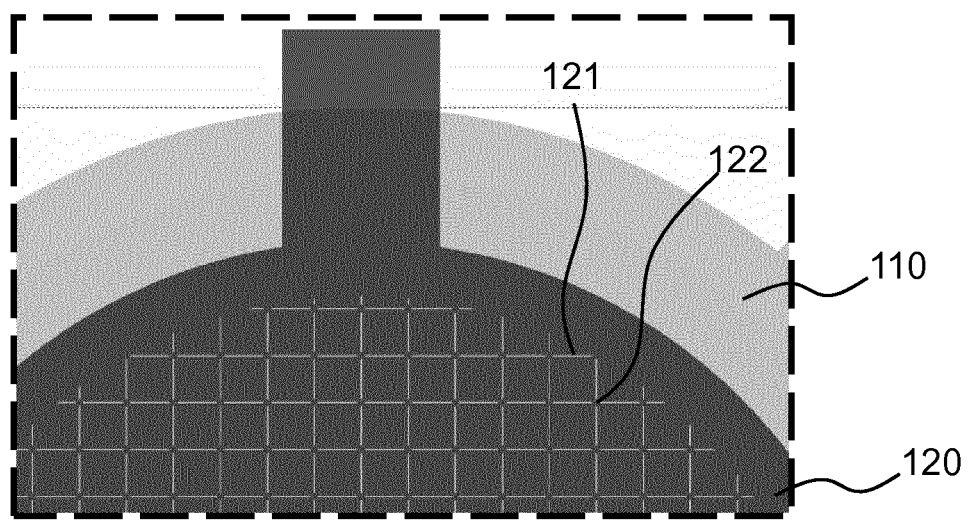
FIG. 7 schematically depicts an aspect of the CMUT transducer array of FIG. 6 in more detail.
Figure 8:
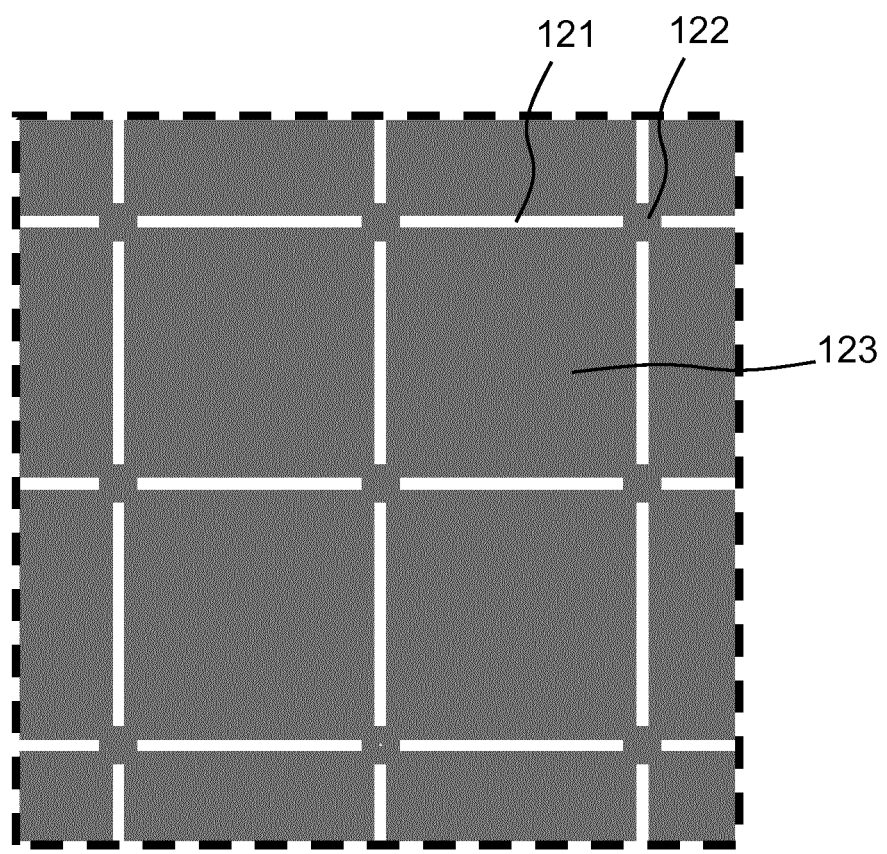
FIG. 8 schematically depicts another aspect of the CMUT transducer array of FIG. 6 in more detail.

FIG. 6 schematically depicts an embodiment according to an alternative invention in which the first electrode arrangement and the second electrode arrangement of the ultrasound transducer array are partitioned into a plurality of sections or regions by respective fuse portions 112, 122. FIG. 7 and FIG. 8 schematically depict magnifications of the dashed regions in FIG. 6. In this embodiment, fuse portions 112 are arranged within each single first electrode 110 and fuse portions 122 are arranged within each single second electrode 120 to partition these electrodes into multiple electrode regions such that only part of the electrode is rendered non-functional upon the occurrence of a short circuit within a CMUT cell 100. This has the advantage that the CMUT cell 100 may still be used even if it does contain a short circuit as large parts of the transducer area remain operational. The fuse portions 112, 122 may be arranged within conductive tracks such as conductive tracks 121 defining a grid of conductive tracks forming the electrode. The fuse portions 112, 122 may be located at junctions or intersections of such conductive tracks such that an electrode region delimited by conductive tracks such as second electrode region 123 delimited by conductive tracks 121 can be electrically isolated from the rest of the electrode by blowing the fuse portions 122 at the junctions of the conductive tracks 121. As many parallel conductive tracks define the electrode, the fuse portions in these conductive tracks have a limited impact on the overall resistivity of the electrode.

In FIG. 6-8, each of the first electrodes 110 and the second electrodes 120 may be partitioned into multiple regions by respective fuse portions 112, 122. However, this is by way of non-limiting example only and it is equally feasible that only one of the first electrode arrangement and the second electrode arrangement is partitioned in this manner.

One or more CMUT transducer arrays according to embodiments of the present invention may be advantageously incorporated into sensing apparatuses such as a pressure sensing apparatus and in particular in a medical imaging apparatus, e.g. an ultrasound imaging apparatus, where the integration of CMUT-based sensing elements can significantly improve the imaging resolution of the apparatus, which for instance improves the detectability of small size objects, e.g. anomalies such as tumours, in the body of a subject under investigation, e.g. a mammalian body such as a human body. In an embodiment, such an apparatus may comprise a CMUT transducer array according to embodiments of the present invention comprising a plurality of CMUT cells 100. Each of the CMUT cells 100 may be individually addressable. Alternatively, appropriate groups of CMUT cells 100, which together form an acoustic element, may be individually addressable at the group level. The CMUT cells 100 or groups of CMUT cells 100 may be arranged in a matrix. In a further embodiment, several CMUT transducer arrays, e.g. CMUT dies may be mounted, e.g. tiled, on a carrier, wherein the multiple CMUT transducer arrays together define a large sensor area. Such an apparatus may for instance comprise several hundreds or thousands of (individually addressable) CMUT cells 100 distributed over one or more CMUT transducer arrays. For example, such a sensing apparatus may comprise an ultrasound probe including one or more CMUT transducer arrays according to an embodiment of the present invention.

Figure 9:
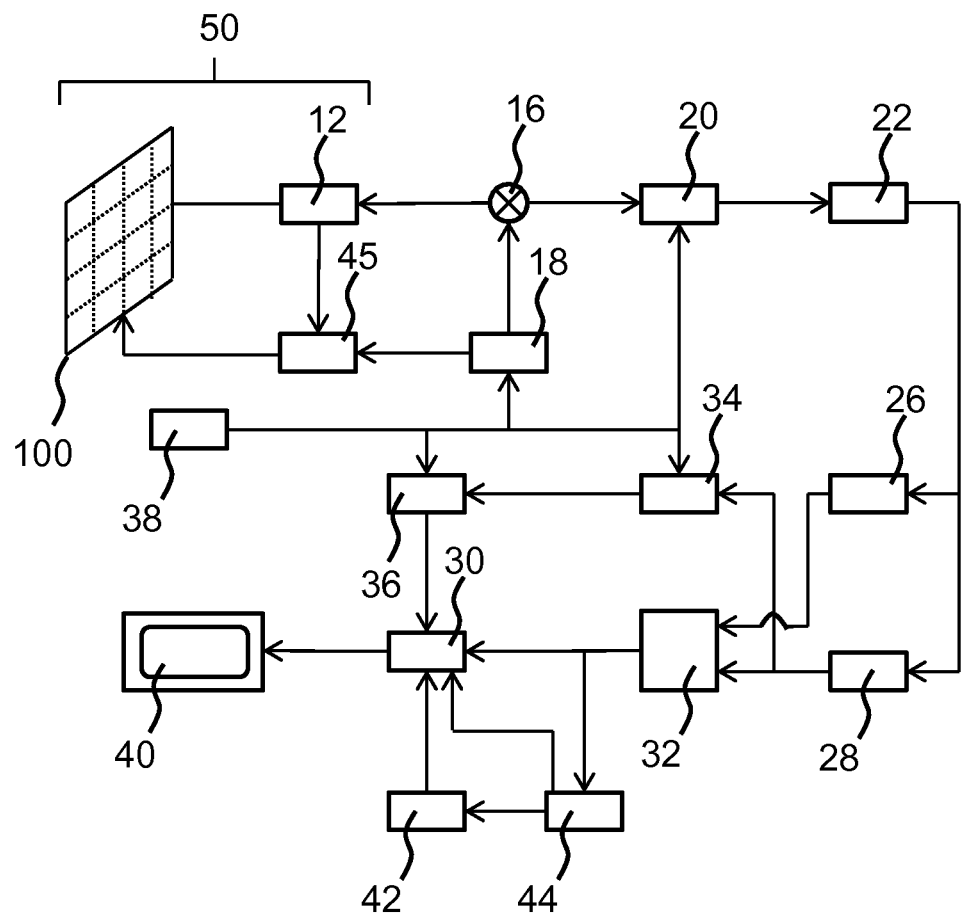
FIG. 9 schematically depicts an ultrasound system according to an example embodiment.

Referring to FIG. 9, an example embodiment of an ultrasound system with an array of CMUT cells 100 (i.e. an ultrasound transducer array) according to an embodiment of the present invention is shown in block diagram form. At least some of the components of the ultrasound system described below may be integrated in a control interface of such an ultrasound system as is well-known per se. Such a control interface may be coupled to a probe 50 or other suitable device including at least one ultrasound transducer array according to an embodiment by a connection cable (not shown).

In FIG. 9 an array of CMUT transducer cells 100 on an IC die is provided as part of an ultrasound probe 50 for transmitting ultrasonic waves and optionally for receiving echo information. The transducer array may be a one- or a two-dimensional array of transducer elements capable of scanning in a 2D plane or in three dimensions for 3D imaging. The ultrasound system may be an ultrasound diagnostic imaging system, typically configured to receive echo information, or may be an ultrasound therapeutic system in which ultrasound pulses are delivered for the treatment of a particular condition, in which case the ultrasound system may not require receiver capability. In the remainder, ultrasound diagnostic imaging system will be described. The skilled person will immediately realize which integers of the ultrasound diagnostic imaging system may be omitted in an ultrasound therapeutic system.

The transducer array is coupled to a microbeam former 12 in the probe 50, e.g. mounted on an integrated interposer region of the IC die, which controls transmission and reception of signals by the CMUT array cells 100. Microbeam formers are capable of at least partial beam forming of the signals received by groups or "patches" of transducer elements for instance as described in US patents U.S. Pat. No. 5,997,479 (Savord et al.), U.S. Pat. No. 6,013,032 (Savord), and U.S. Pat. No. 6,623,432 (Powers et al.)

The microbeam former 12 is coupled by the probe cable, e.g. a coaxial wire, to a transmit/receive (T/R) switch 16 which switches between transmission and reception and protects the main beam former 20 from high energy transmit signals when a microbeam former is not present or used and the transducer array is operated directly by the main system beam former 20. The transmission of ultrasonic beams from the transducer array under control of the microbeam former 12 is directed by a transducer controller 18 coupled to the microbeam former by the T/R switch 16 and the main system beam former 20, which receives input from the user's operation of the user interface or control panel 38. One of the functions controlled by the transducer controller 18 is the direction in which beams are steered and focused. Beams may be steered straight ahead from (orthogonal to) the transducer array, or at different angles for a wider field of view. The transducer controller 18 may be coupled to control a DC bias control 45 for the CMUT array. For instance, the DC bias control 45 sets DC bias voltage(s) that are applied to the CMUT cells 100 of an ultrasound transducer array.

Figure 2:
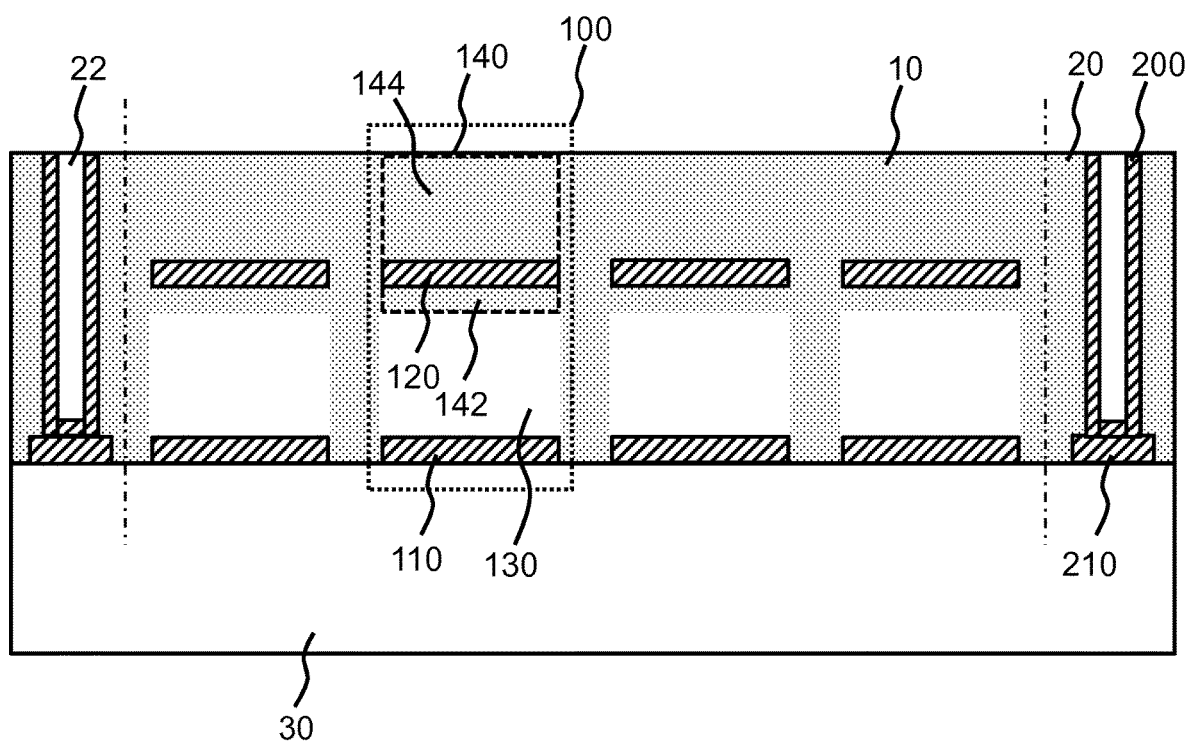
FIG. 2 schematically depicts a cross-section of a known CMUT transducer array.

The partially beam-formed signals produced by the microbeam former 12 are forwarded to the main beam former 20 where partially beam-formed signals from individual patches of transducer elements are combined into a fully beam-formed signal. For example, the main beam former 20 may have 128 channels, each of which receives a partially beam-formed signal from a patch of dozens or hundreds of CMUT transducer cells 112 (see FIG. 1-3) or piezoelectric elements. In this way the signals received by thousands of transducer elements of a transducer array can contribute efficiently to a single beam-formed signal.

The beam-formed signals are coupled to a signal processor 22. The signal processor 22 can process the received echo signals in various ways, such as band pass filtering, decimation, I and Q component separation, and harmonic signal separation which acts to separate linear and nonlinear signals so as to enable the identification of nonlinear (higher harmonics of the fundamental frequency) echo signals returned from tissue and microbubbles.

The signal processor 22 optionally may perform additional signal enhancement such as speckle reduction, signal compounding, and noise elimination. The band pass filter in the signal processor 22 may be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals are coupled to a B-mode processor 26 and optionally to a Doppler processor 28. The B-mode processor 26 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in US Patents U.S. Pat. No. 6,283,919 (Roundhill et al.) and U.S. Pat. No. 6,458,083 (Jago et al.)

The Doppler processor 28, if present, processes temporally distinct signals from tissue movement and blood flow for the detection of the motion of substances, such as the flow of blood cells in the image field. The Doppler processor 28 typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor 28 receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B-mode (and Doppler) processor(s) 28 are coupled to a scan converter 32 and a multiplanar reformatter 44. The scan converter 32 arranges the echo signals in the spatial relationship from which they were received in a desired image format. For instance, the scan converter 32 may arrange the echo signal into a two dimensional (2D) sector-shaped format, or a pyramidal three dimensional (3D) image.

The scan converter 32 can overlay a B-mode structural image with colors corresponding to motion at points in the image field with their Doppler-estimated velocities to produce a color Doppler image which depicts the motion of tissue and blood flow in the image field. The multiplanar reformatter 44 will convert echoes which are received from points in a common plane in a volumetric region of the body into an ultrasonic image of that plane, for instance as described in US Patent U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.)

The 2D or 3D images are coupled from the scan converter 32, multiplanar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B-mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name.

The user interface is also coupled to the transmit controller 18 to control the generation of ultrasound signals from the transducer array and hence the images produced by the transducer array and the ultrasound system. The user interface is also coupled to the multiplanar reformatter 44 for selection and control of the planes of multiple multiplanar reformatted (MPR) images which may be used to perform quantified measures in the image field of the MPR images.

As will be understood by the skilled person, the above embodiment of an ultrasonic diagnostic imaging system is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the microbeam former 12 and/or the Doppler processor 28 may be omitted, the ultrasound probe 50 may not have 3D imaging capabilities and so on. Other variations will be apparent to the skilled person.

Some aspects of the present application may be summarized by the following clauses:

Clause 1: An ultrasound transducer array comprising a plurality of CMUT (capacitive micromachined ultrasound transducer) cells (100), each CMUT cell comprising a substrate (300) carrying a first electrode (110) of a first electrode arrangement, wherein at least part of the substrate being spatially separated from a flexible membrane including a second electrode (120) of a second electrode arrangement by a gap (130), at least one of the first electrode and the second electrode being electrically insulated from said gap by at least one dielectric layer (311, 313), wherein at least one of the first electrode arrangement and the second electrode arrangement is partitioned into a plurality of sections interconnected by respective fuse portions (112, 122), wherein each first electrode (110) or second electrode (120) is a patterned electrode comprising a grid of conductive tracks (111, 121) each including at least one fuse portion (112, 122). Both the first electrodes and the second electrodes may be patterned in this manner. In this manner, each electrode of the CMUT cells of the ultrasound transducer array may be partitioned into multiple sections in order to provide the capability to electrically isolate faulty sections, i.e. sections that have developed a short circuit, from the remainder of the electrode such that the electrodes remains operable despite the presence of a short circuit in the CMUT cell. Each fuse portion may be located at an intersection of said grid.

Clause 2: An ultrasound transducer array according to clause 1, wherein each fuse portion (112, 122) is located at an intersection of said grid.

Clause 3: The ultrasound transducer array of clause 1 or 2, wherein each first electrode (110) and each second electrode (120) is a patterned electrode comprising a grid of said conductive tracks (111, 121).

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An ultrasound transducer array comprising:
a plurality of CMUT (capacitive micromachined ultrasound transducer) cells, each CMUT cell comprising a substrate carrying a first electrode of a first electrode arrangement, wherein at least part of the substrate being spatially separated from a flexible membrane including a second electrode of a second electrode arrangement by a gap, wherein at least one of the first electrode or the second electrode is electrically insulated from the gap by at least one dielectric layer, wherein at least one of the first electrode arrangement or the second electrode arrangement is partitioned into a plurality of sections interconnected by respective fuse portions, wherein:
the first electrode arrangement comprises a plurality of rows of first electrodes, the first electrodes in each row being interconnected by respective first fuse portions; and
the second electrode arrangement comprises a plurality of columns of second electrodes, the second electrodes in each column being interconnected by respective second fuse portions different from the first fuse portions, wherein each row and column is individually addressable.

2. The ultrasound transducer array of claim 1, wherein at least one of the first fuse portions and/or at least one of the second fuse portions has a sheet resistance not exceeding 1Ω/□(Ohm per square).

3. The ultrasound transducer array of claim 1, wherein the at least one dielectric layer comprises a first dielectric layer in between the gap and the first electrode and a second dielectric layer in between the gap and the second electrode.

4. The ultrasound transducer array of claim 1, wherein at least one of the first fuse portions and/or at least one of the second fuse portions is strip-shaped.

5. The ultrasound transducer array of claim 1, wherein at least one of the first fuse portions and/or at least one of the second fuse portions is bow tie-shaped.

6. The ultrasound transducer array of claim 1, wherein the first fuse portions extend in a different direction from the second fuse portions.

7. The ultrasound transducer array of claim 1, wherein the first fuse portions comprise at least one first fuse portion disposed between two CMUT cells of the plurality of CMUT cells.

8. The ultrasound transducer array of claim 1, wherein the second fuse portions comprise at least one second fuse portion disposed between two CMUT cells of the plurality of CMUT cells.

9. The ultrasound transducer array of claim 1, wherein a CMUT cell of the plurality of CMUT cells includes two first fuse portions extending along a first direction and positioned on opposite sides of the CMUT cell.

10. The ultrasound transducer array of claim 9, wherein the CMUT cell includes two second fuse portions extending along a different, second direction and positioned on opposite sides of the CMUT cell.

11. An ultrasound probe comprising the ultrasound transducer array of claim 1.

12. An ultrasound system comprising the ultrasound transducer array of claim 1, or the ultrasound probe of claim 11, the ultrasound system further comprising a power supply conductively coupled to the first electrode arrangement and the second electrode arrangement.

13. The ultrasound system of claim 12, wherein the ultrasound system is an ultrasound diagnostic imaging system or an ultrasound therapeutic system.

\* \* \* \* \*